(12) United States Patent  
Matharu et al.

(10) Patent No.: US 8,481,780 B2
(45) Date of Patent: *Jul. 9, 2013

(54) POLYMORPHS OF BROMFENAC SODIUM AND METHODS FOR PREPARING BROMFENAC SODIUM POLYMORPHS

(71) Applicant: Johnson Matthey Public Limited Company, London (GB)

(72) Inventors: Saroop Singh Matharu, Shirley, MA (US); Gurijala Venu Reddy, Lancaster, MA (US); James J. Mencel, North Wales, PA (US); Xiaoyong Sun, Acton, MA (US)

(73) Assignee: Johnson Matthey Public Limited Company, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/626,304

(22) Filed: Sep. 25, 2012

(65) Prior Publication Data

US 2013/0023588 A1    Jan. 24, 2013

Related U.S. Application Data

(63) Continuation of application No. 12/891,007, filed on Sep. 27, 2010, now Pat. No. 8,299,295.

(60) Provisional application No. 61/251,925, filed on Oct. 15, 2009.

(51) Int. Cl.
 *C07C 229/00* (2006.01)
(52) U.S. Cl.
 USPC .......................................................... 562/441

(58) Field of Classification Search
 None
 See application file for complete search history.

(56) References Cited

U.S. PATENT DOCUMENTS

| 4,045,576 | A | 8/1977 | Welstead, Jr. et al. |
| 4,126,635 | A | 11/1978 | Welstead, Jr. et al. |
| 4,182,774 | A | 1/1980 | Welstead, Jr. et al. |
| 4,683,242 | A | 7/1987 | Poser |
| 4,910,225 | A | 3/1990 | Ogawa et al. |
| 8,129,431 | B2 | 3/2012 | Sawa et al. |
| 2003/0232871 | A1 | 12/2003 | Sheikh et al. |
| 2004/0082647 | A1 | 4/2004 | Babiak et al. |
| 2005/0002859 | A1 | 1/2005 | Marnett et al. |
| 2006/0052432 | A1 | 3/2006 | Remenar et al. |
| 2006/0205969 | A1 | 9/2006 | Xu et al. |
| 2007/0043050 | A1 | 2/2007 | Nunes et al. |
| 2008/0220441 | A1 | 9/2008 | Birnbaum et al. |
| 2008/0318968 | A1 | 12/2008 | Martin et al. |

FOREIGN PATENT DOCUMENTS

| EP | 0 221 753 A2 | 5/1987 |
| EP | 0 326 915 B1 | 8/1989 |
| EP | 1 586 316 A1 | 10/2005 |
| WO | WO-01/15677 A2 | 3/2001 |

(Continued)

OTHER PUBLICATIONS

Nolan et al., "The topical anti-inflammatory and analgesic properties of bromfenac in rodents," *Agents and Actions*, vol. 25, 1/2, 1988, pp. 77-85.

(Continued)

*Primary Examiner* — Johann R Richter
*Assistant Examiner* — Jennifer C Sawyer
(74) *Attorney, Agent, or Firm* — RatnerPrestia

(57) ABSTRACT

Different polymorphs of bromfenac sodium may be prepared and interconverted using crystallization/recrystallization, drying and/or hydration techniques.

32 Claims, 7 Drawing Sheets

FOREIGN PATENT DOCUMENTS

| | | |
|---|---|---|
| WO | WO-2009/050251 A2 | 4/2009 |
| WO | WO-2009/139817 A2 | 11/2009 |
| WO | WO-2009/141144 A1 | 11/2009 |
| WO | WO-2010/005958 A2 | 1/2010 |

OTHER PUBLICATIONS

Guengerich et al., "Applying Mechanisms of Chemical Toxicity to Predict Drug Safety," *Chem. Res. Toxicol.*, vol. 20, 2007, pp. 344-369.

Da Silva et al., "The Chemistry of Isatins: a Review from 1975 to 1999," *J. Braz. Chem. Soc.*, vol. 12, No. 3, 2001, pp. 273-324.

Welstead, Jr., et al. "Antiinflammatory Agents. 1. Synthesis and Antiinflammatory Activity of 2-Amino-3-benzoylphenylacetic Acid," Journal of Medicinal Chemistry, vol. 22, No. 9, 1979, pp. 1074-1079.

Xia et al., "Synthesis of Bromfenac Sodium Salt," *Journal of China Pharmaceutical University*, vol. 34, No. 5, 2003, pp. 405-406.

Walsh et al., "Antiinflammatory Agents. 3. Synthesis and Pharmacological Evaluation of 2-Amino-3-benzoylphenylacetic Acid and Analogues," *Journal of Medicinal Chemistry*, vol. 27, No. 11, Nov. 1984, pp. 1379-1388.

Sugasawa et al., "Aminohaloborane in Organic Synthesis. 1. Specific Ortho Substitution Reaction of Anilines," *J. Am. Chem. Soc.*, vol. 100, No. 15; Jul. 19, 1978, pp. 4842-4852.

Lo et al., "Synthesis of 2-Amino-3-benzoylphenylacetic Acid," *Journal of Heterocyclic Chemistry*, vol. 17, No. 8, Dec. 1980, pp. 1663-1664.

Sugasawa et al, "Aminohaloborane in Organic Synthesis. 2. Simple Synthesis of Indoles and 1-Acyl-3-indolinones Using Specific Ortho α-Chloroacetylation of Anilines," *J. Org. Chem.*, vol. 44, No. 4, 1979, pp. 578-586.

Carpenter et al, "Nitro Musks. I. Isomers, Homologs, and Analogs of Musk Ambrette," *J. Org. Chem.*, 1951, vol. 16, No. 4, pp. 586-617.

Dobbs et al, "Total Synthesis of Indoles from *Tricholoma* Species via Bartoli/Heteroaryl Radical Methodologies," *J. Org. Chem.*, vol. 66, 2001, pp. 638-641.

Kollmar et al., "2-Amino-3-Fluorobenzoic Acid," *Organic Syntheses*, Coll. vol. 10, p. 23 (2004); vol. 79, p. 196 (2002).

Tilstam et al., "A mild and efficient dehydrogenation of indolines," *Tetrahedron Letters*, Vo. 42, 2001, pp. 5385-5387.

Mawatari et al., "Fluorimetric determination of isatin in human urine and serum by liquid chromatography postcolumn photoirradiation," *The Analyst*, vol. 126, 2001, pp. 33-36.

Xibrom™ (bromfenac ophthalmic solution)0.09%, Full Prescribing Information, Revised Mar. 2010, Copyright © ISTA Pharmaceuticals, Inc. All rights reserved. XIB581-5/10.

British Combined Search and Examination Report dated Feb. 17, 2012 from British Patent Application No. 1121765.0.

POLYMORPHS OF BROMFENAC SODIUM AND METHODS FOR PREPARING BROMFENAC SODIUM POLYMORPHS

CROSS-REFERENCE TO RELATED APPLICATIONS

This application is a continuation of U.S. patent application Ser. No. 12/891,007, filed Sep. 27, 2010, and claims priority to U.S. Provisional Patent Application No. 61/251,925, filed Oct. 15, 2009, the disclosures of both which are incorporated herein by reference in their entireties for all purposes.

FIELD OF THE INVENTION

The present invention relates to novel polymorphs of bromfenac sodium, to novel, reproducible processes for their preparation, and to pharmaceutical compositions containing such polymorphs.

DISCUSSION OF THE RELATED ART

Bromfenac sodium (which is the sodium salt of 2-amino-3-(4-bromobenzoyl)phenyl acetic acid, also sometimes referred to as sodium 2-amino-3-(4-bromobenzoyl)phenyl acetate sesquihydrate, having the empirical formula $C_{15}H_{11}BrNNaO_3 \cdot 1.5H_2O$) is a non-steroidal anti-inflammatory drug (NSAID) with analgesic properties. It was initially marketed as an oral suspension under the trade name DURACT but was withdrawn from the United States market in 1998 due to drug-induced hepatotoxicity leading to acute liver failure. Currently, bromfenac sodium is sold as an ophthalmic solution under the brand name XIBROM. The Food and Drug Administration approved this product in 2005 for use in ophthalmic surgery including postoperative inflammation, reduction of pain after cataract and refractive surgery and management of macular edema after cataract surgery. XIBROM ophthalmic solution contains 1.035 mg bromfenac sodium, equivalent to 0.9 mg bromfenac free acid per mL of solution, giving a 0.09% sterile topical ophthalmic formulation with a pH of 8.3.

A survey of the literature on bromfenac sodium did not provide any reference to its crystal structure or the possibility of different polymorphs. Information about the solid-state properties of a drug substance is important. For example, different forms may have significantly different solubilities. Also the handling and stability of a drug substance may depend critically on the solid form.

Polymorphism is defined as "the ability of a compound to crystallize in more than one distinct crystal species" and different crystal arrangements of the same chemical composition are termed polymorphs. Polymorphs of the same compound arise due to differences in the internal arrangement of atoms and have different free energies and therefore different physical properties such as solubility, chemical stability, melting point, density, flow properties, bioavailability and so forth.

BRIEF SUMMARY OF THE INVENTION

It has now been discovered that bromfenac sodium can be prepared in three well-defined and consistently reproducible crystalline forms, as well as mixtures of certain of these crystalline forms. Moreover, reliable and scalable methods for interconverting these crystalline forms have been developed. The bromfenac sodium polymorphs provided by the present invention are useful active ingredients in pharmaceutical formulations.

In one aspect of the invention, bromfenac sodium Form I is provided, preferably substantially free of any other physical forms of bromfenac sodium. This polymorph of bromfenac sodium is a highly crystalline consistent polymorph and is a sesquihydrate that is stable. Bromfenac sodium Form I may be prepared by a process comprising crystallizing or recrystallizing bromfenac sodium from a solvent mixture comprising water, at least one dialkoxyalkane, and at least one anti-solvent. The present invention permits bromfenac sodium Form I to be obtained in highly pure form; in particular, bromfenac sodium Form I that has very low levels of residual sodium hydroxide and other reagents (carried over from the synthesis of the bromfenac sodium), organic solvents, process impurities, and bromfenac sodium degradation products may be prepared.

In another aspect of the invention, bromfenac sodium Form II is provided. Bromfenac sodium Form II is a hydrate of bromfenac sodium containing less than 1.5 moles of water per mole of bromfenac sodium (e.g., about 1 mole water per mole of bromfenac sodium).

In still another aspect of the invention, bromfenac sodium Form III is provided. Bromfenac sodium Form III is a non-hydrated polymorph of bromfenac sodium that may be prepared by a process comprising crystallizing or recrystallizing bromfenac sodium from a solvent mixture comprising water and at least one alcohol. Another method for preparing bromfenac sodium Form III comprises treating 7-(4-bromobenzoyl)indol-2-one with sodium hydroxide in a mixture of water, at least one alcohol, and at least one aromatic hydrocarbon to obtain a bromfenac sodium reaction mixture and combining at least one anti-solvent with the bromfenac sodium reaction mixture.

Mixtures comprised of bromfenac sodium Form I and bromfenac sodium Form II are also furnished by the present invention. Such mixtures may be prepared by crystallizing or recrystallizing bromfenac sodium from a solvent mixture comprising water, at least one dialkoxyalkane, and at least one anti-solvent to give an initial solid product and drying the initial solid product under vacuum.

Also provided by the present invention is a method for converting bromfenac sodium Form I into bromfenac sodium Form II, comprising drying bromfenac sodium Form I under vacuum.

The present invention also provides a method for converting a material selected from bromfenac sodium Form I, bromfenac sodium Form II or a mixture of bromfenac sodium Form I and bromfenac sodium Form II into bromfenac sodium Form III, comprising crystallizing or recrystallizing the material from a solvent mixture comprised of water and at least one alcohol.

In another aspect of the invention, bromfenac sodium Form II is converted into bromfenac sodium Form I by a process comprising hydrating the bromfenac sodium Form II.

A method for converting bromfenac sodium Form III into bromfenac sodium Form I is additionally provided by the present invention, wherein the method comprises crystallizing or recrystallizing the bromfenac sodium Form III from a solvent mixture comprised of water, at least one dialkoxyalkane, and at least one anti-solvent such as a dialkylether to yield an intermediate product containing less than 1.5 moles of water per mole of bromfenac sodium and hydrating the intermediate product.

In still another aspect of the invention, bromfenac sodium Form I may be converted into bromfenac sodium Form III by a process comprising crystallizing or recrystallizing bromfenac sodium Form I from a solvent mixture comprising water and at least one alcohol.

A method for converting bromfenac sodium Form III into bromfenac sodium Form II is further provided by the present invention, wherein the method comprises crystallizing or recrystallizing bromfenac sodium Form III from a solvent mixture comprised of water, at least one dialkoxyalkane, and at least one anti-solvent such as a dialkyl ether to obtain an intermediate product and drying the intermediate product under vacuum.

DETAILED DESCRIPTION OF CERTAIN EMBODIMENTS OF THE INVENTION

The bromfenac sodium to be used as a starting material for the preparation of the bromfenac sodium polymorphs which are the subject of the present invention may be synthesized using any of the methods known in the art. For example, bromfenac sodium can be produced as described in Walsh et al., *Journal of Medicinal Chemistry*, Volume 27, pages 1379-1388 (1984) or U.S. Pat. No. 4,683,242 (Example 74), each of which is incorporated herein by reference in its entirety for all purposes.

Figure 1:
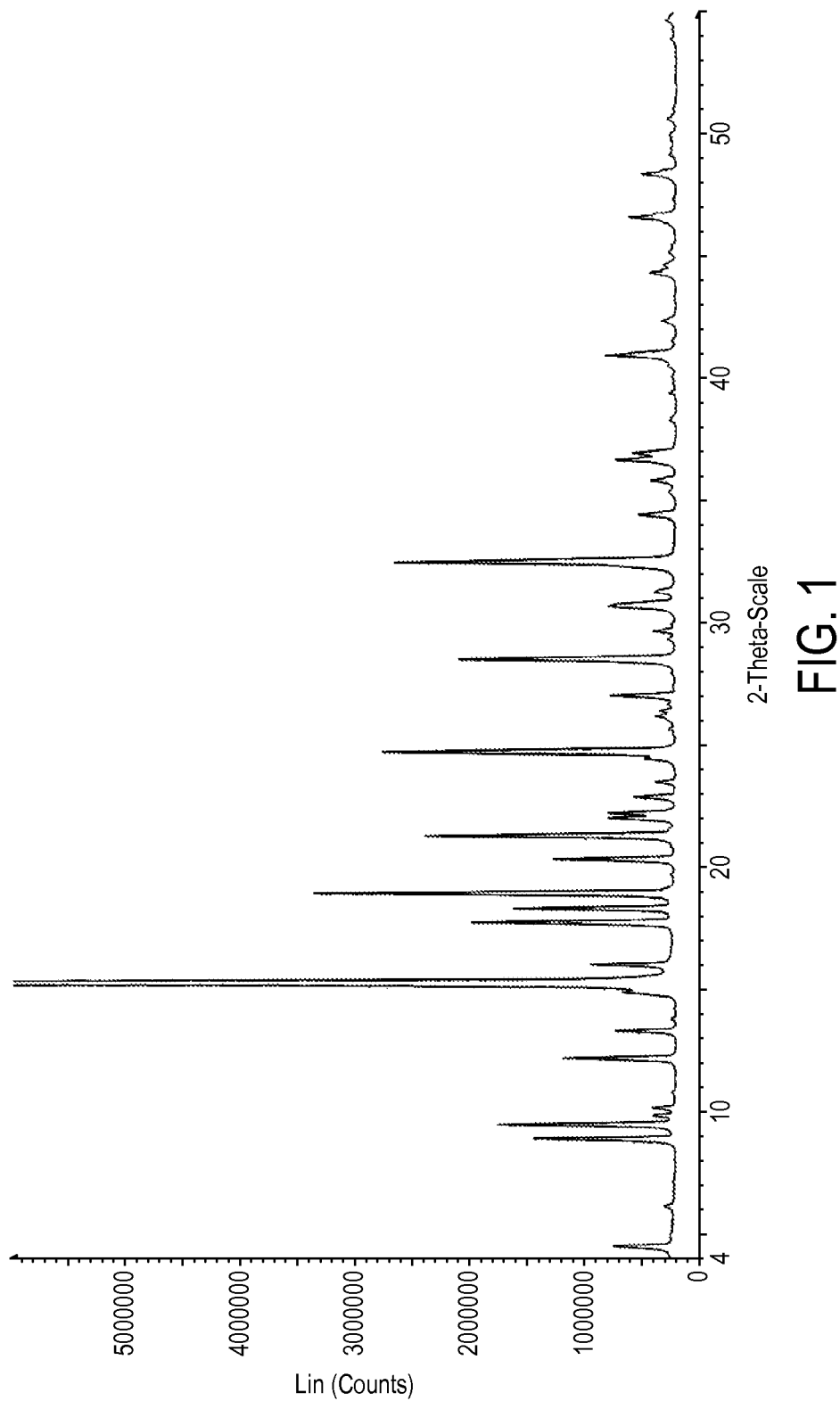
FIG. 1 is a representative x-ray powder diffraction (XRPD) pattern of bromfenac sodium Form I in accordance with the invention.
Figure 2:
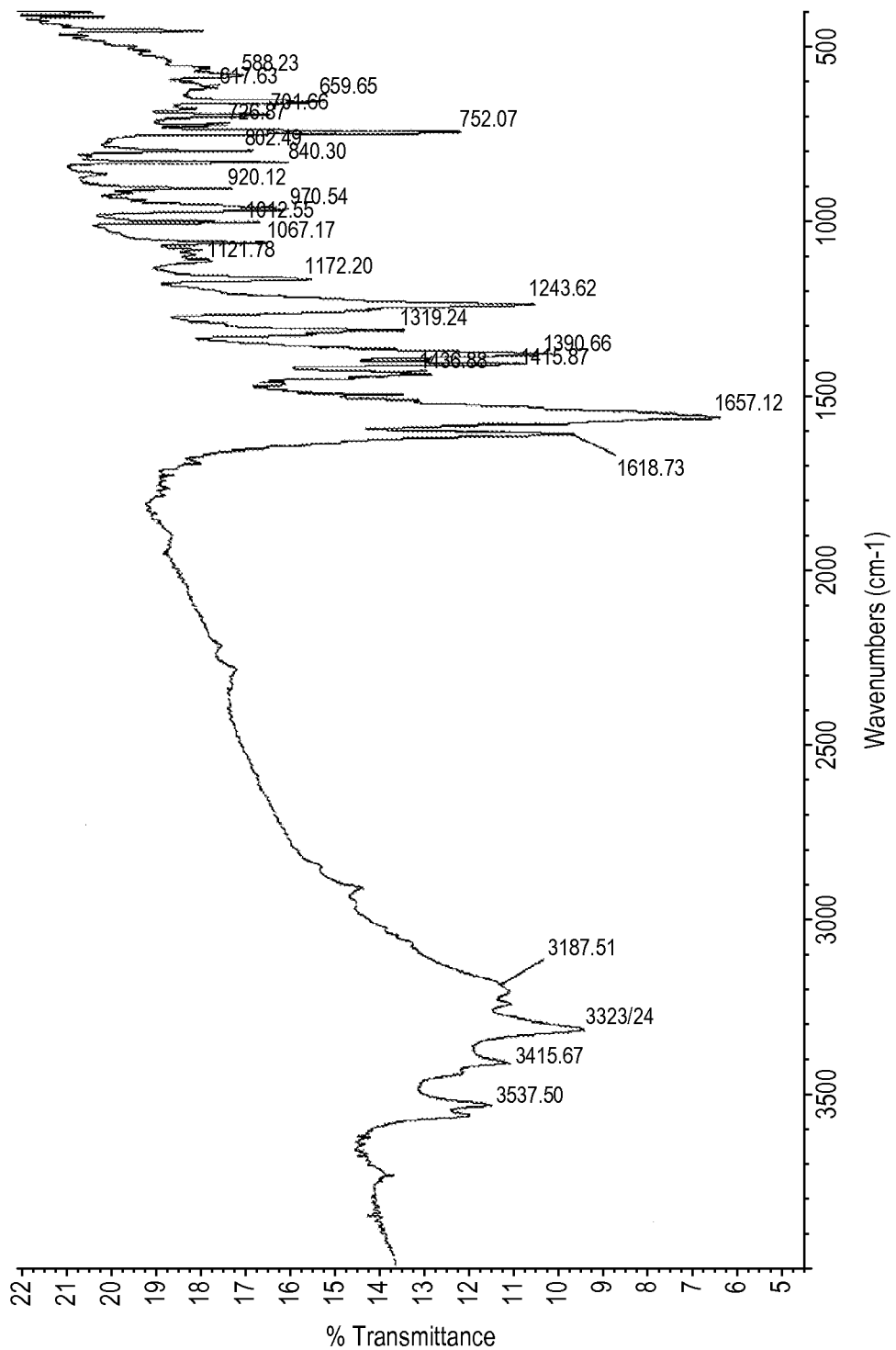
FIG. 2 is an FT-IR spectrum of a representative sample of bromfenac sodium Form I in accordance with the invention.

Bromfenac sodium Form I is a highly crystalline polymorph of bromfenac provided by the present invention which is a stable sesquihydrate. FIG. 1 is a representative x-ray powder diffraction (XRPD) pattern of bromfenac sodium Form I. Table A lists a d-spacing/% intensity pattern typical of bromfenac sodium Form I (peaks having a relative intensity of <2.0% are not listed). The powder x-ray diffraction pattern of bromfenac sodium Form I may have main peaks expressed as 2-theta at about 4.4, 8.8, 9.4, 12.1, 15.2, 15.9, 17.6, 18.2, 18.8, 20.2, 21.2, 24.7, 28.4, and 32.4 degrees. FIG. 2 shows an FT-IR spectrum of a representative sample of bromfenac sodium Form I. In one embodiment, the bromfenac sodium Form I is purified and isolated such that it is substantially free of any other physical forms of bromfenac sodium. "Substantially free" in the context of the present invention means that the powder x-ray diffraction pattern does not exhibit any visible peaks associated with other bromfenac sodium polymorphs.

The present invention enables the preparation of bromfenac sodium Form I which is not only substantially free from any other physical forms of bromfenac sodium but also has a very high level of chemical purity. That is, bromfenac sodium Form I prepared in accordance with the invention may be substantially free of process impurities (i.e., impurities that are structurally related to bromfenac sodium and that are carried through or produced during the synthetic process, such as precursors of the bromfenac sodium), degradation products of bromfenac sodium, as well as substances unrelated to bromfenac sodium such as residual solvents, metals or reagents carried through from the process of manufacture. For example, in one embodiment, the bromfenac sodium Form I product does not contain more than 0.15% AUC (alternatively, not more than 0.10% AUC) of any process impurity or bromfenac sodium degradation product, as measured by high pressure liquid chromatography. As another example, the present invention enables the preparation of bromfenac sodium Form I that is substantially free of residual sodium hydroxide, as evidenced by a relatively low pH when the bromfenac sodium Form I is dissolved in water. High levels of residual sodium hydroxide have been found to increase the hygroscopicity of the bromfenac sodium Form I product (i.e., it exhibits a greater tendency to absorb more than 1.5 moles of water per mole of bromfenac sodium). Preferably, the pH of such a solution is not more than 11, or, more preferably, not more than 10.6. In another aspect, the bromfenac sodium Form I may contain less than 200 ppm or less than 150 ppm organic solvent in total, as measured by gas chromatography. In still another aspect, the bromfenac sodium Form I may contain less than 100 ppm aluminum, boron, and manganese in total and/or less than 30 ppm of each of these elements, as measured by Inductively Coupled Plasma Optical Emission Spectroscopy (ICP-OES).

TABLE A

| Angle 2-theta | d value, Angstrom | Intensity % |
| --- | --- | --- |
| 15.2 | 5.80 | 100.0 |
| 18.8 | 4.69 | 12.5 |
| 17.6 | 5.00 | 10.9 |
| 24.7 | 3.59 | 10.3 |
| 21.2 | 4.17 | 9.3 |
| 20.2 | 4.37 | 9.1 |
| 32.4 | 2.75 | 9.1 |
| 8.8 | 10.0 | 8.9 |
| 9.4 | 9.38 | 7.6 |
| 28.4 | 3.12 | 7.4 |
| 18.2 | 4.85 | 7.3 |
| 12.1 | 7.27 | 5.8 |
| 15.9 | 5.55 | 5.7 |
| 4.4 | 20.01 | 5.1 |
| 22.1 | 4.00 | 4.5 |
| 13.2 | 6.68 | 3.8 |
| 21.9 | 4.04 | 3.8 |
| 30.6 | 2.91 | 3.2 |
| 40.9 | 2.20 | 3.0 |
| 25.9 | 3.42 | 2.3 |
| 29.6 | 3.01 | 2.3 |
| 31.2 | 2.85 | 2.3 |
| 26.5 | 3.35 | 2.2 |
| 10.0 | 8.76 | 2.2 |
| 23.4 | 3.79 | 2.0 |

Bromfenac sodium Form I may be prepared by a process comprising crystallizing and/or recrystallizing bromfenac sodium from a solvent mixture comprising water, at least one dialkoxyalkane, and at least one anti-solvent. The bromfenac sodium may be an initial or crude reaction product obtained by synthesizing bromfenac sodium from a suitable precursor such as hydrolysis of the corresponding indolone. The bromfenac sodium starting material may also be, for example, bromfenac sodium Form III. In addition to producing bromfenac sodium Form I crystals which are substantially free of any other bromfenac sodium polymorphs, such crystallization and recrystallization processes provide the further advantage of facilitating the removal or reduction of other impurities in the bromfenac sodium starting material (e.g., unreacted or residual reagents, byproducts, etc.). For example, the bromfenac sodium starting material may be a sample of bromfenac sodium Form I that is contaminated with chemical impurities and/or minor amounts of one or more other bromfenac polymorphs, wherein the recrystallization is effective to improve the chemical and/or polymorphic purity of the sample.

In one aspect of the invention, the crystallization or recrystallization is carried out by dissolving the starting bromfenac sodium in a mixture of water and dialkoxyalkane to prepare an initial solution. The solvent mixture may be heated to facilitate dissolution of the bromfenac sodium, e.g., to a temperature of from about 40 to about 90° C. One or more anti-solvents are then added to the initial solution and the resulting mixture cooled (with or without agitation, such as by stirring), thereby allowing crystals of the desired bromfenac sodium Form I to precipitate from solution. For example, the mixture may be cooled to a temperature of from about −10 to about 20° C. Seed crystals of bromfenac sodium Form I may be added to promote or accelerate the crystallization process. If the initial sample of bromfenac sodium is contaminated with difficulty soluble impurities, it may be desirable to filter the initial solution and/or the mixture following addition of the anti-solvent (before cooling) to remove such impurities. The bromfenac sodium Form I crystals may be collected and separated from the mother liquor by any conventional separation technique such as filtration, decantation or centrifugation, then subjected to further purification or processing steps such as washing and/or drying if so desired. The separated mother liquor may be further treated to recover additional bromfenac sodium Form I crystals and/or purified solvent for reuse in a crystallization or recrystallization step. These techniques may be readily adapted for use in connection with the practice of the other crystallization/recrystallization processes described herein for other bromfenac sodium polymorphs.

Suitable dialkoxyalkanes include, but are not limited to, hydrocarbons substituted with two or more $C_1$-$C_4$ alkoxy groups such as 1,2-dimethoxyethane, 1,2-dimethoxypropane, 2,2-dimethoxypropane, diethoxymethane, 1,1-diethoxyethane, 1,2-diethoxyethane, and the like and mixtures thereof. As used herein, the term anti-solvent refers to a solvent in which the desired product (i.e., the product being crystallized or recrystallized) is insoluble or essentially insoluble; the function of an anti-solvent thus is to reduce the solubility of the product in the solvent mixture and enhance the yield of precipitated crystals thereby recovered. Suitable anti-solvents include dialkylethers, particularly $C_4$-$C_{10}$ dialkyl ethers such as diethyl ether, dipropyl ether, diisopropyl ether, tert-butyl methyl ether, sec-butyl methyl ether, and the like and mixtures thereof. In one particularly advantageous embodiment, the solvent mixture is comprised of water, 1,2-dimethoxyethane, and tert-butyl methyl ether.

If the bromfenac sodium starting material is contaminated with undesirably high levels of residual sodium (e.g., sodium hydroxide) carried over from a indolone hydrolysis procedure used to prepare the bromfenac sodium starting material, the following procedure may be followed in order to obtain bromfenac sodium Form I that is free or substantially free of residual sodium contaminants. The bromfenac sodium starting material is dissolved in an aqueous dialkoxyalkane mixture (e.g., 10-20% v/v water in 1,2-dimethoxyethane (3-8 mL/g bromfenac sodium)) at a temperature (e.g., 55-80° C.) effective to form a solution (the mixture may be de-aerated by bubbling an inert gas such as nitrogen through the mixture prior to heating). The solution is then permitted to settle until an aqueous layer forms (the aqueous layer will contain at least a portion of the residual sodium contaminants). The organic layer is separated from the aqueous layer. While the organic layer is still warm (to avoid premature crystallization of the bromfenac sodium), a filtration may be performed to remove insoluble impurities. The organic layer is then concentrated (under vacuum, for example) to form a wet slurry. The wet slurry is then combined with an anti-solvent such as tert-butyl methyl ether. Crystalline, purified bromfenac sodium Form I is thereafter recovered by filtration and may be washed (with additional quantities of anti-solvent, for example) and dried (taking care to avoid over-drying, such that fewer than 1.5 moles water per mole bromfenac sodium are present in the final product).

In another aspect of the invention, the bromfenac sodium starting material is dissolved in a mixture of 8-12% v/v water in 1,2-dimethoxyethane (10-14 mL/g bromfenac sodium starting material) at 50-75° C. to form a solution. The solution may be filtered while still warm to remove any insoluble impurities, then combined with a mixture of 15-25% v/v 1,2-dimethoxyethane in tert-butyl methyl ether (8-12 mL/g bromfenac sodium starting material). Cooling the resulting mixture to a temperature of 0-15° C. over several (e.g., 4-8) hours provides bromfenac sodium Form I as a highly crystalline product, which may be separated from the mother liquor and dried. If needed (for example, where the drying conditions used to remove the organic solvent from the crystalline product result in fewer than 1.5 molecules of water per molecule of bromofenac sodium), hydration of the product thereby obtained may be carried out to ensure that the stable sesquihydrate is the exclusive polymorph present.

Hydration may be effected by exposing the product to water, particularly water vapor. For example, the product may be placed within an enclosed chamber under vacuum and water vapor (in the form of moist air or moist nitrogen, for instance) may be bled into the enclosed chamber. Alternatively, the product may be exposed to a moist atmosphere at approximately atmospheric pressure within an enclosed chamber containing a source of liquid water.

If so desired, the above-described procedures for producing bromfenac sodium Form I may be adapted and modified so as to provide a product that is a mixture of bromfenac sodium Form I and bromfenac sodium Form II. Bromfenac sodium Form II is a polymorph that is believed to be a monohydrate of bromfenac sodium, i.e., containing one water molecule per molecule of bromfenac sodium, and characterized by a powder x-ray diffraction pattern having main peaks expressed as 2-theta at about 11.3, 14.4, 16.5, 17.3, 18.5, 19.4, 20.7, 21.0, 22.7, 29.0, 31.8, 34.1 and 36.1 degrees. Drying the crystalline product initially obtained in the crystallization process described above under a vacuum results in the removal of some water of hydration from the sesquihydrate and the formation of the Form II polymorph, as evidenced by XRPD. The vacuum drying conditions may be adjusted so as to vary the Form II polymorph content of the product obtained. For example, higher drying temperatures, lower pressures, and increased drying times will generally all increase the amount of bromfenac sodium Form II present. It is believed that such parameters may be selected so as to provide bromfenac sodium Form II in substantially pure form (i.e., substantially free of any bromfenac sodium Form I or any other polymorph). However, since bromfenac sodium Form II is not stable, it should be protected from atmospheric moisture or other sources of water to protect it from hydration and thus conversion to another polymorph such as bromfenac sodium Form I.

In another aspect of the invention, bromfenac sodium Form I may be prepared from bromfenac sodium Form III by a process comprising heating (preferably, after de-aeration) a mixture of bromfenac sodium Form III, water and a dialkoxyalkane (e.g., 1,2-dimethoxyethane) for a time and at a temperature effective to form an organic layer and an aqueous layer. Following separation of the aqueous layer and, optionally, filtration, the organic layer may be concentrated and combined with one or more anti-solvents (e.g., a dialkylether) effective to cause precipitation/crystallization of the desired bromfenac sodium Form I. The bromfenac sodium Form I thus obtained in solid form may be separated from the mother liquor by filtration, decantation, centrifugation or like method, washed (with anti-solvent, for example) if so desired, and dried (as noted above, overly harsh drying conditions should be avoided, if substantially pure bromfenac sodium Form I is desired).

Figure 3:
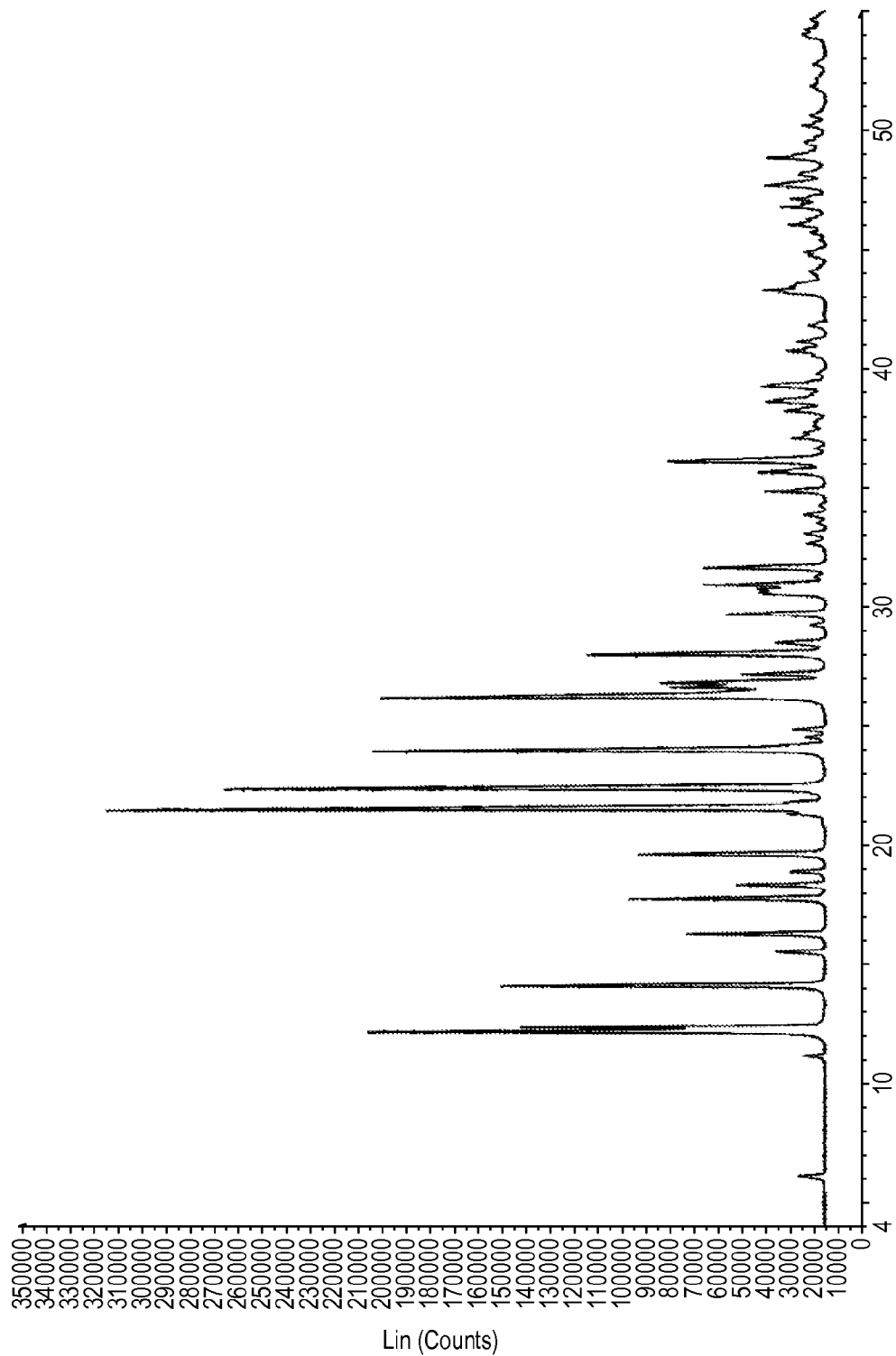
FIG. 3 is a representative x-ray powder diffraction (XRPD) pattern of bromfenac sodium Form III in accordance with the invention.
Figure 4:
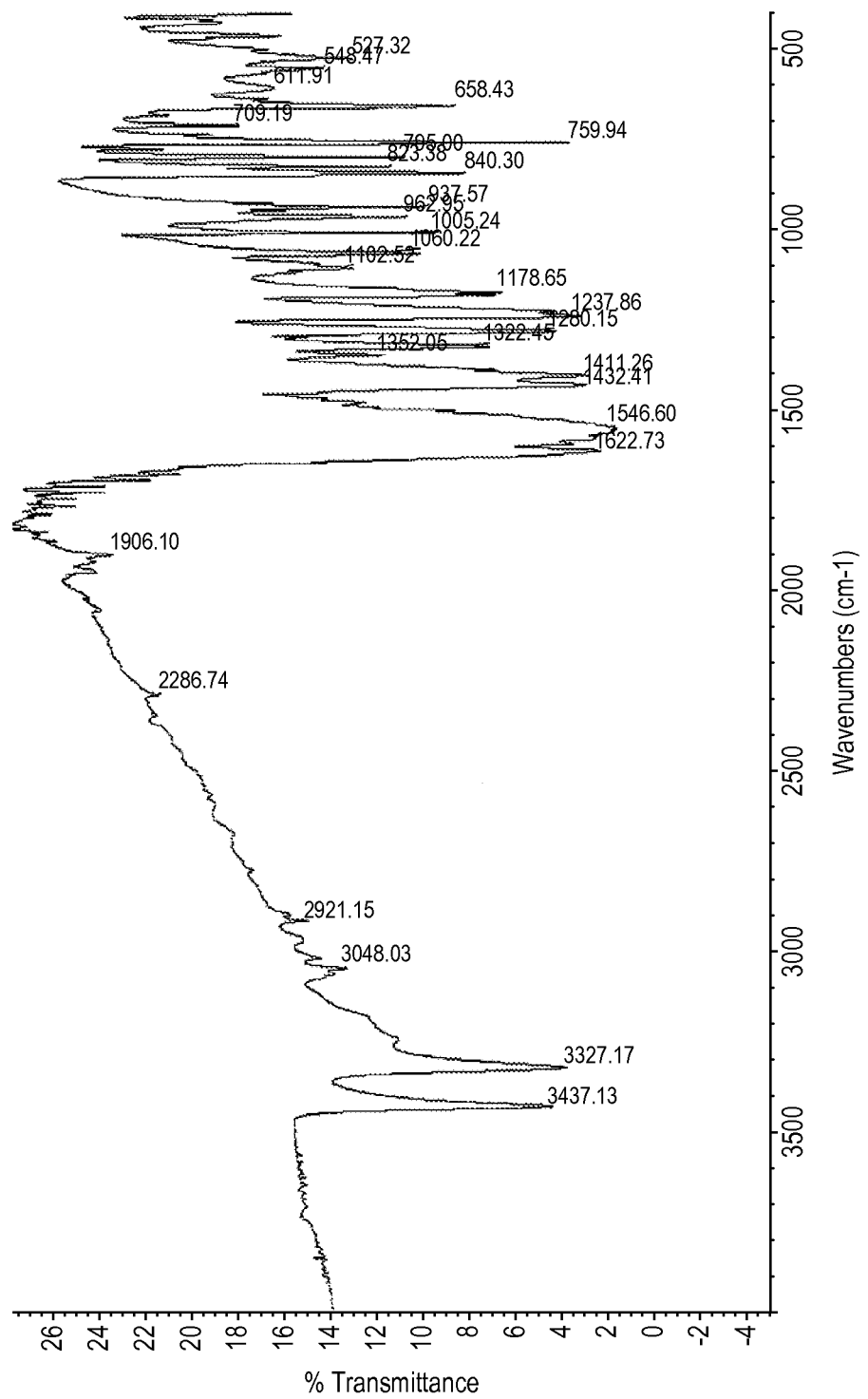
FIG. 4 is an FT-IR spectrum of a representative sample of bromfenac sodium Form III in accordance with the invention.

Bromfenac sodium Form III is a crystalline polymorph of bromfenac provided by the present invention which does not contain any water of hydration. The rate of dissolution in water is significantly lower than the dissolution rate observed for bromfenac sodium Form I or other hydrated forms of bromfenac sodium. Bromfenac sodium Form III has been found to be stable and exhibits little or no tendency to adsorb water (the water content of a sample subjected to wet nitrogen "hydration" conditions in a 30-35° C. vacuum oven (5 mm Hg) for 17 hours did not change). FIG. 3 is a representative x-ray powder diffraction (XRPD) pattern of bromfenac sodium Form III. Table B lists a d-spacing/% intensity pattern typical of bromfenac sodium Form III. The powder x-ray diffraction pattern of bromfenac sodium Form III may have main peaks expressed as 2-theta at about 12.2, 12.4, 14.1, 17.8, 19.6, 21.6, 22.4, 24.0, 26.3 and 28.1 degrees. FIG. 4 shows the FT-IR spectrum of a representative sample of bromfenac sodium Form III. In one embodiment, the bromfenac sodium Form III is purified and isolated such that it is substantially free of any other physical forms of bromfenac sodium.

TABLE B

| Angle 2-theta | d value, Angstrom | Intensity % |
|---|---|---|
| 21.6 | 4.11 | 100.0 |
| 22.4 | 3.96 | 85.1 |
| 12.2 | 7.26 | 66.5 |
| 24.0 | 3.70 | 66.0 |
| 26.3 | 3.39 | 65.0 |
| 14.1 | 6.28 | 49.3 |
| 12.4 | 7.15 | 46.8 |
| 28.1 | 3.17 | 38.3 |
| 17.8 | 4.99 | 32.8 |
| 19.6 | 4.52 | 31.6 |
| 26.8 | 3.32 | 28.8 |
| 36.2 | 2.48 | 27.8 |
| 16.3 | 5.44 | 25.3 |
| 26.7 | 3.34 | 24.8 |
| 31.7 | 2.82 | 23.3 |
| 31.0 | 2.88 | 23.3 |
| 29.7 | 3.00 | 20.2 |
| 18.3 | 4.84 | 18.9 |
| 27.2 | 3.27 | 18.3 |
| 35.7 | 2.51 | 16.2 |
| 39.4 | 2.29 | 15.7 |
| 43.4 | 2.08 | 15.6 |
| 30.7 | 2.91 | 15.5 |
| 47.8 | 1.90 | 15.2 |
| 34.9 | 2.57 | 15.2 |

TABLE B-continued

| Angle 2-theta | d value, Angstrom | Intensity % |
|---|---|---|
| 49.0 | 1.86 | 15.0 |
| 38.7 | 2.32 | 14.3 |
| 28.5 | 3.12 | 14.0 |
| 15.5 | 5.71 | 13.8 |
| 46.9 | 1.94 | 13.3 |
| 38.3 | 2.35 | 12.8 |

Bromfenac sodium Form III may be prepared by a process comprising crystallizing and/or recrystallizing bromfenac sodium from a solvent mixture comprising water and at least one alcohol. This result was surprising, in view of the fact that water is present in the solvent mixture and thus would be expected to be incorporated into the bromfenac sodium crystals being formed during crystallization/recrystallization. The at least one alcohol may include one or more $C_1$-$C_4$ alcohols, in particular at least one of ethanol or 2-propanol. Solvent mixtures comprised of water and 2-propanol (containing, for example, about 2 to about 8% v/v water) have been found to be particularly suitable for use as crystallization or recrystallization solvents to obtain bromfenac sodium Form III polymorph in substantially pure form. The bromfenac sodium starting material may, for example, be bromfenac sodium Form I, bromfenac sodium Form II, and/or a mixture of the Form I and Form II polymorphs.

Another method of preparing bromfenac sodium Form III involves treating 7-(4-bromobenzoyl)indol-2-one with a sodium-containing base such as sodium hydroxide in a medium comprised of water, at least one alcohol, and at least one aromatic hydrocarbon to obtain a reaction mixture that is then combined with at least one anti-solvent. It may be desirable to heat the reaction mixture prior to being combined with the anti-solvent at a temperature (e.g., about 50 to about 90° C.) and for a time (e.g., about 3 to about 25 hours) effective to convert the indol-2-one to the corresponding sodium salt. Following such heating, the reaction mixture may be cooled somewhat (e.g., to about 20 to about 40° C.) before adding the anti-solvent. Adding the anti-solvent will effect crystallization or precipitation of the desired bromfenac sodium Form III in solid form, which may be then separated from the mother liquor by filtration, centrifugation, decantation or other such separation method, washed with suitable solvent (e.g., an anti-solvent such as tert-butyl methyl ether), and dried. Suitable alcohols include $C_1$-$C_4$ alcohols such as methanol, ethanol, 1-propanol, 2-propanol, 1-butanol, 2-butanol, tert-butanol and the like and mixtures thereof. Suitable aromatic hydrocarbons include aromatic hydrocarbons containing only one aromatic ring and optionally substituted with one or more substituents other than hydrogen, such as $C_1$-$C_4$ alkyl groups or halogen. Toluene and xylene are examples of useful aromatic hydrocarbons. Suitable anti-solvents include, but are not limited to, alkylethers such as tert-butyl methyl ether. The amount of anti-solvent employed preferably is sufficient to effect precipitation of at least the majority of the bromfenac sodium present in the reaction mixture. In one embodiment of the invention, the solvents and reagent solutions (e.g., sodium hydroxide solution) are de-aerated prior to use by, for example, bubbling an inert gas such as nitrogen through the solvent or reagent solution.

Figure 7:
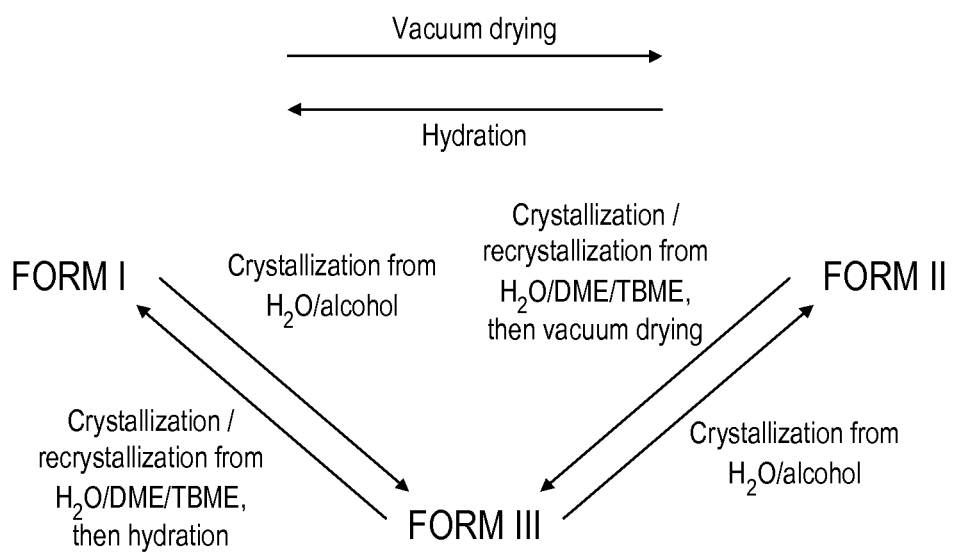
FIG. 7 illustrates in schematic form certain of the polymorph interconversions capable of being realized through the invention.

The present invention further provides processes for converting one polymorph of bromfenac sodium into a different bromfenac polymorph. FIG. 7 illustrates in schematic form certain of the interconversions that are possible. The particular solvent systems listed in FIG. 7 are for illustrative purposes only and are not meant to be limiting in any way. Also, as used herein, the terms "crystallization" (or "crystallizing") and "recrystallization" (or "recrystallizing") are intended to include not only processes in which a complete solution is achieved at some point in the process but also processes in which the material being crystallized or recrystallized is never completely solubilized at any point. That is, the interconversions may be capable of being achieved using processes wherein at least a portion of the material being converted or processed remains undissolved (i.e., the material/solvent mixture takes the form of a slurry of solids in a liquid medium, rather than a complete solution).

As previously mentioned, bromfenac sodium Form I may be converted, at least partially, into bromfenac sodium Form II by drying bromfenac sodium Form I under vacuum. Also, as previously described, bromfenac sodium Form II can be converted into bromfenac sodium Form I by hydrating the bromfenac sodium Form II.

Additionally, a material selected from bromfenac sodium Form I, bromfenac sodium Form II or a mixture of bromfenac sodium Form I and bromfenac sodium Form II may be converted into bromfenac sodium Form III by a method comprising crystallizing or recrystallizing the material from a solvent mixture comprised of water and at least one alcohol. Suitable alcohols and crystallization/recrystallization conditions will generally be similar to those previously mentioned in connection with the preparation of bromfenac sodium Form III from bromfenac sodium.

A method for converting bromfenac sodium Form III into bromfenac sodium Form I is also provided by the present invention. The method comprises crystallizing or recrystallizing the bromfenac sodium Form III from a solvent mixture comprised of water, at least one dialkoxyalkane, and at least one anti-solvent such as a dialkyl ether to yield an intermediate product containing less than 1.5 moles of water per mole of bromfenac sodium and hydrating the intermediate product. Suitable dialkoxyalkanes, dialkyl ethers, and hydration conditions will generally be similar to those previously in connection with the preparation of bromfenac sodium Form I from bromfenac sodium.

The bromfenac sodium polymorphs provided by the present invention are useful as active ingredients in pharmaceutical formulations employed in the treatment of various diseases or conditions, particularly inflammatory conditions. The polymorphs may be utilized as individual, substantially pure polymorphs (i.e., substantially free from other physical forms of bromfenac sodium) or as admixtures of two or more different bromfenac sodium polymorphs. Medicinal uses for bromfenac sodium and analogous benzoylphenyl acetic acid salts are well known in the art and are described, for example, in U.S. Pat. Nos. 4,045,576; 4,126,635; 4,182,774; 4,683,242; and 4,910,225 (the disclosure of each of which is incorporated herein by reference in its entirety for all purposes). The bromfenac sodium polymorph or polymorphs in accordance with the present invention may be formulated together with one or more excipients such as carriers, solvents, preservatives, stabilizers, surfactants, pH adjusting agents, diluents, fillers, or the like, as may be desired or needed for purposes of the intended end use. The pharmaceutical formulation may be in solid or liquid form, such as a tablet, capsule, solution, suspension, ointment or the like.

For example, the bromfenac sodium polymorphs of the present invention can be used as active ingredients in topically administrable therapeutic compositions for inflammatory eye disease as well as nasal or otic disease.

The ophthalmic compositions can be prepared in the form of eye drops, eye ointments and so on in the same manner as various known compositions for topical administration to the eye. Thus, a bromfenac sodium polymorph or bromfenac sodium polymorph mixture in accordance with the present invention can be made up into an aqueous or non-aqueous solution or mixed with an ointment base suited for ophthalmic use. An aqueous base such as those generally used in the production of ophthalmic preparations, for example sterile distilled water, may be suitably used as the aqueous base. The pH of the ophthalmic preparation is adjusted, if needed, to a level suited for topical administration to the eye. In one embodiment, an appropriate buffer is added in adjusting the pH. The pH of the ophthalmic preparation should be selected with due consideration paid to the stability and topical eye irritativity of the bromfenac sodium active ingredient, among others. In one embodiment, the stability of an aqueous composition containing the bromfenac sodium is enhanced by incorporating a water-soluble polymer and sulfite, and adjusting the pH to 6.0-9.0, preferably about 7.5-8.5. Illustrative suitable water-soluble polymers include polyvinyl pyrrolidone, carboxypropylcellulose, hydroxyethylcellulose, hydroxypropylcellulose, polyvinyl alcohol, sodium salts of polyacrylic acid and the like. The water-soluble polymer concentration may be in the range of about 0.1 to 10 w/w %, based on the total weight of the solution. Suitable sulfites include sodium sulfite, potassium sulfite, and the like, with the sulfite concentration typically being in the range of about 0.1 to 1.0 w/w %, based on the total weight of the solution. The pH adjustment is generally conducted with sodium hydroxide or hydrochloric acid, for instance, and a buffer solution may be formed by combined use of, for example, sodium acetate, sodium borate or sodium phosphate and acetic acid, boric acid or phosphoric acid, respectively. The ophthalmic composition may contain one or more additional pharmaceutically active ingredients, such as an anti-inflammatory agent of another kind, an analgesic and/or an antimicrobial.

In preparing such ophthalmic compositions, one or more of an isotonizing agent, a microbicidal agent or preservative, a chelating agent, a thickening agent and so forth may be added to the compositions in accordance with the general practice of ophthalmic preparation manufacture. Suitable isotonizing agents include, among others, sorbitol, glycerine, polyethylene glycol, propylene glycol, glucose and sodium chloride. Illustrative preservatives include para-oxybenzoic acid esters, benzyl alcohol, parachloro-meta-xylenol, chlorocresol, phenetyl alcohol, sorbic acid and salts thereof, thimerosal, chlorobutanol, and the like. The chelating agent may be, for example, sodium edetate, sodium citrate or a sodium salt of condensed phosphoric acid. In preparing an ophthalmic composition in the form of an eye ointments, the ointment base can be selected from among petrolatum, polyethylene glycol, carboxymethylcellulose sodium, and the like.

The ophthalmic composition may be prepared by incorporating the bromfenac sodium polymorph or polymorph mixture in a base or vehicle for topical application to the eye. To prepare a liquid preparation, the concentration of the active ingredient may range from about 0.001% to about 10% by weight and is preferably in the range of about 0.01% to about 5% by weight. An ointment may be prepared by using the bromfenac sodium polymorph or polymorph mixture in a concentration from about 0.001% to about 10% by weight, preferably about 0.01% to about 5% by weight. The ophthalmic composition may, for example, be administered in accordance with any of the following schedules. In the form of eye-drops, one to several drops per dose are instilled with a frequency of once to 4 times a day according to the clinical condition. The dosage may be adjusted according to symptoms.

EXAMPLES

Example 1

Preparation of Form III Polymorph of the Sodium Salt of 2-amino-3-(4-bromobenzoyl)phenylacetic acid (Bromfenac Sodium Form III)

The solvents (toluene and ethanol) used for the reaction were de-aerated by bubbling nitrogen gas prior to use. A solution of 7-(4-bromobenzoyl)indol-2-one (221 g, 0.7 mol; prepared in accordance with Walsh, D. A.; Moran, H. W.; Shamblee, D. A.; Uwaydah, I. M.; Welstead, Jr., W. J., Sancilio, L. F.; Dannenburg, W. N. J. Med. Chem. 1984, 27, 1379-1388) in de-aerated ethanol (0.4 Kg) and de-aerated toluene (1.4 Kg) was prepared and further de-aerated by bubbling nitrogen gas. A solution of sodium hydroxide (64 g, 1.61 mol) in water (65 g) was prepared, de-aerated by bubbling nitrogen gas and added, in one portion, to the stirred 7-(4-bromobenzoyl)indol-2-one solution. The resulting mixture was further de-aerated and while maintaining nitrogen gas atmosphere it was heated at 68° C. to 72° C. for 15 h.

The mixture was then cooled to 28° C., tert-butyl methyl ether (1.7 Kg) added and after stirring for 2 h, the solid product was filtered. The filtered product was washed with tert-butyl methyl ether (3×0.4 Kg) and dried on the filter at ambient temperature under the vacuum filtration conditions for 3 h to give the Form III polymorph, as indicated by XRPD analysis, of the sodium salt of 2-amino-3-(4-bromobenzoyl)phenylacetic acid (284 g) as a yellow solid.

Example 2

Preparation of Form I Polymorph of the Sodium Salt of 2-amino-3-(4-bromobenzoyl)phenylacetic acid (Conversion of Form III Polymorph into Form I Polymorph)

A 284 g portion of sodium salt of 2-amino-3-(4-bromobenzoyl)phenylacetic acid, Form III polymorph (prepared in accordance with Example 1) was charged into a reactor and a mixture of water (208 g) and 1,2-dimethoxyethane (1.0 Kg) added. The stirred suspension was de-aerated by bubbling nitrogen gas, then heated at 65° C. to 71° C. for 30 minutes. The resulting mixture was allowed to settle for 10 minutes and after removal of the lower aqueous layer, the organic layer was cooled to 67° C. and filtered. The solution was concentrated in vacuo at 36° C. to a damp slurry. To the wet slurry was added tert-butyl methyl ether (1.0 Kg) and the mixture stirred for 1 h. The resulting crystalline product was filtered, washed with tert-butyl methyl ether (3×0.4 Kg) and dried on the filter under vacuum filtration conditions for 3 h to give the Form I polymorph, as indicated by XRPD analysis, of the sodium salt of 2-amino-3-(4-bromobenzoyl)phenylacetic acid, sesquihydrate (243 g) as a yellow solid.

Example 3

Recrystallization of Form I Polymorph of the Sodium Salt of 2-amino-3-(4-bromobenzoyl)phenylacetic acid A 242 g portion of the sodium salt of 2-amino-3-(4-bromobenzoyl)phenylacetic acid sesquihydrate, Form I polymorph was charged into a reactor and a mixture of water (262 g) and 1,2-dimethoxyethane (2.1 Kg) added. The stirred suspension was de-aerated by bubbling nitrogen gas, then heated at 65° C. to 70° C. for 10 minutes or until a solution was obtained. The resulting solution was cooled to 68° C. and filtered into a jacketed vessel maintained at 60±5° C. A solution of 1,2-dimethoxyethane (0.4 Kg) in tert-butyl methyl ether (1.3 Kg) was prepared and charged while maintaining the temperature at 60±5° C. The stirred mixture was then cooled to 10° C. over approximately 6 hours and maintained at 6° C. to 10° C. for 1 h. The resulting crystalline product was filtered, washed with tert-butyl methyl ether (2×0.8 Kg) and dried on the filter under vacuum filtration conditions for 1 h at ambient temperature to give Form I polymorph, as indicated by XRPD analysis, of the sodium salt of 2-amino-3-(4-bromobenzoyl)phenylacetic acid, sesquihydrate (148 g) as a yellow solid with 99.95% chemical purity by HPLC.

Sodium Salt of 2-amino-3-(4-bromobenzoyl)phenylacetic acid, sesquihydrate, Form I Polymorph Analytical Data $^1$H-NMR (300 MHz, DMSO-$d_6$) δ (ppm) 3.26 (2H, s), 6.46 (1H, dd, J=7.9 Hz and 7.3 Hz), 7.08 (1H, dd, J=8.1 Hz and 1.3 Hz), 7.15 (1H, d, J=7.1 Hz), 7.49 (2H, d, J=8.7 Hz), 7.71 (2H, d, J=8.7 Hz), 7.96 (2H, bs, exchanges with $D_2O$). $^{13}$C-NMR (300 MHz, DMSO-$d_6$) δ (ppm) 197.0, 174.2, 151.7, 139.4, 135.2, 131.4, 131.1, 130.6, 126.5, 124.4, 116.7, 114.0 and 44.9. HRMS (ES) calculated for carboxylate ion $C_{15}H_{11}BrNO_3^-$ 331.9922 $[M]^+$ and 333.9902 $[M]^+$. found 331.9907 $[M]^+$ and 333.9893 $[M]^+$. FT-IR (KBr) 3538, 3416, 3323, 3250-2900 (br), 1618, 1567, 1437, 1416, 1391, 1319, 1244, 1172, 1067, 1013, 971, 920, 840, 802 and 752 $cm^{-1}$. Analysis, calculated for $C_{15}H_{11}BrNO_3Na.1.5H_2O$: C, 47.02; H, 3.68; N, 3.66. Br, 20.85. Found: C, 47.13; H, 3.62; N, 3.80; Br, 20.35. Water content by Karl Fischer titration, calculated for sesquihydrate: 7.05%. Found, 7.2%. XRPD characteristic peaks expressed as degrees 2-theta at approximately 4.4, 8.8, 9.4, 12.1, 15.2, 15.9, 17.6, 18.2, 18.8, 20.2, 21.2, 24.7, 28.4 and 32.4.

Example 4

Preparation of a Mixture of Form I and Form II Polymorphs of the Sodium Salt of 2-amino-3-(4-bromobenzoyl)phenylacetic acid (Conversion of Form I Polymorph into a Mixture of Form I and Form II Polymorphs)

The sodium salt of 2-amino-3-(4-bromobenzoyl)phenylacetic acid sesquihydrate, Form I polymorph (148 g) was dried under vacuum (29 in Hg) at 33° C. for 6 h and then under vacuum (1.2 mm Hg to 1.6 mm Hg) at 30° C. to 32° C. for 12 h to give a mixture of Form I and Form II polymorphs, as indicated by XRPD analysis, of the sodium salt of 2-amino-3-(4-bromobenzoyl)phenylacetic acid (143 g) as a yellow solid.

Figure 5:
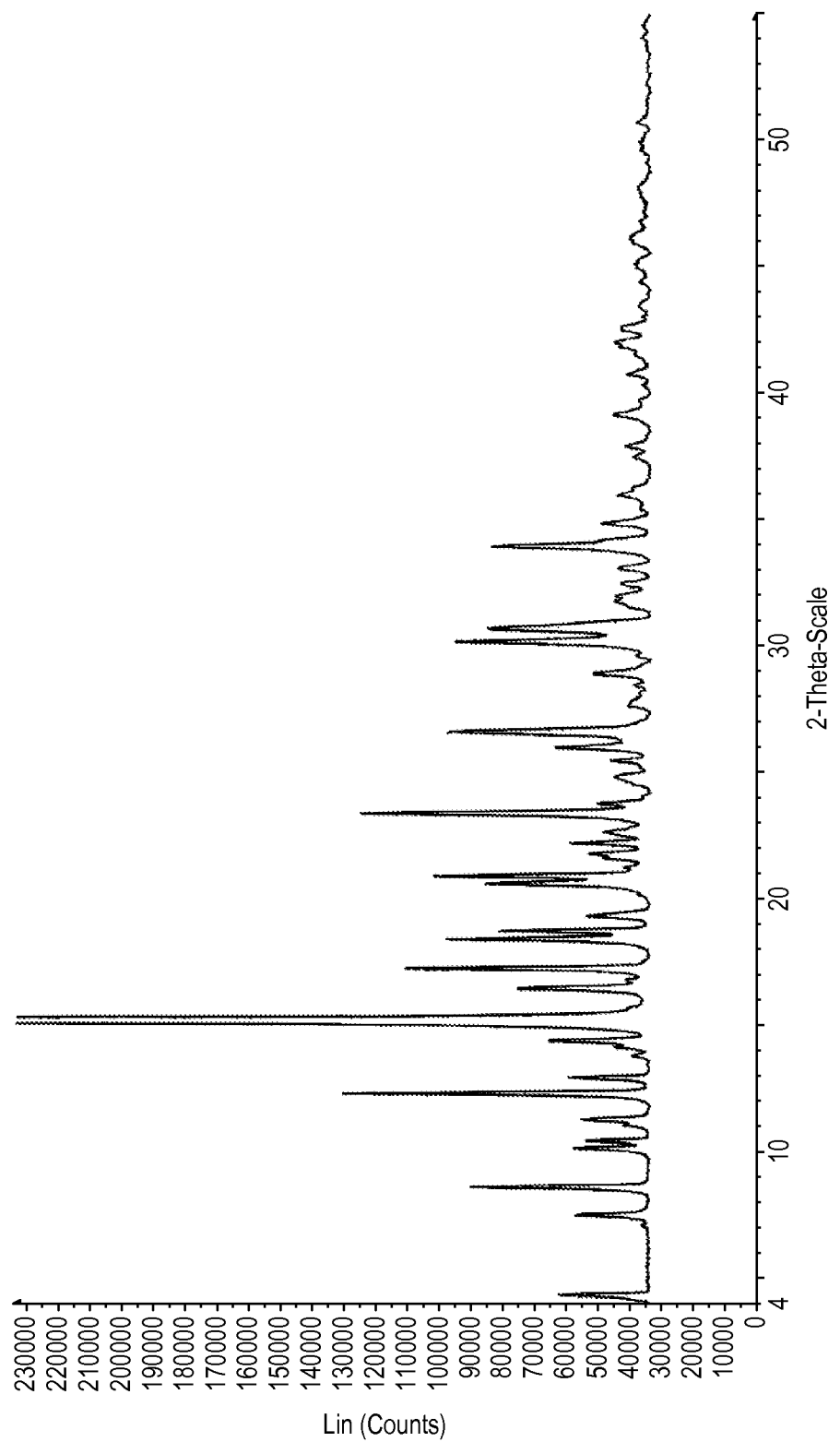
FIG. 5 is an x-ray powder diffraction (XRPD) pattern of a mixture of bromfenac sodium Form I and bromfenac sodium Form II in accordance with the invention.
Figure 6:
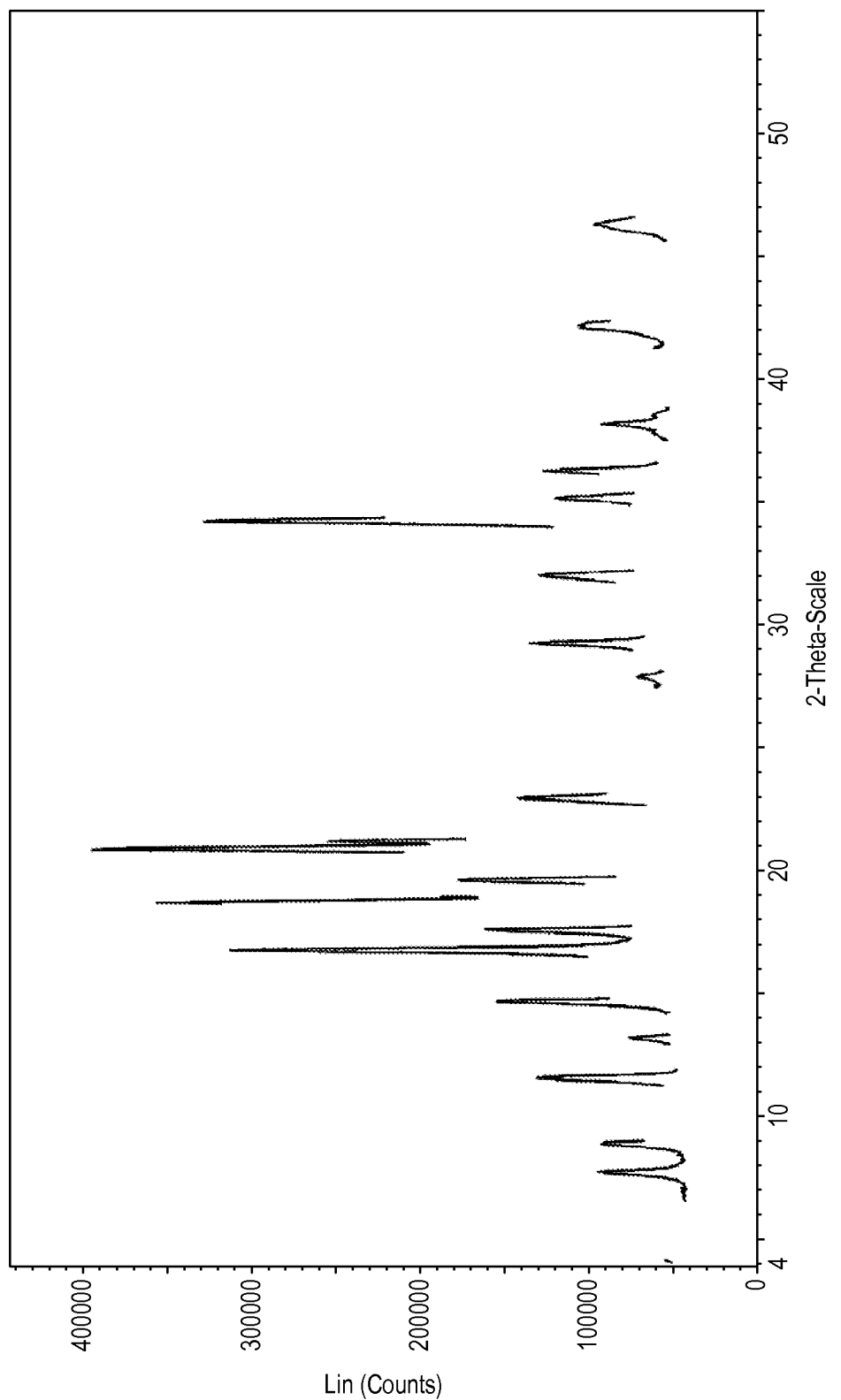
FIG. 6 is a deduced XRPD pattern for bromfenac sodium Form II in accordance with the invention.

FIG. 5 shows the XRPD pattern of a representative sample of a mixture of the Form I and Form II polymorphs of bromfenac sodium. A characteristic d-spacing/% intensity pattern for such a mixture is listed in Table C (only the peaks having a relative intensity >2.0% are listed). FIG. 6 shows the deduced XRPD pattern for bromfenac sodium Form II (i.e., the main peaks attributable to the Form II polymorph). Table D lists the characteristic d-spacing/% intensity pattern attributable to bromfenac sodium Form II in such a mixture.

TABLE C

| Angle 2-theta | d value, Angstrom | Intensity % |
| --- | --- | --- |
| 15.2 | 5.80 | 100.0 |
| 12.3 | 7.18 | 9.5 |
| 23.4 | 3.79 | 8.9 |
| 17.2 | 5.13 | 7.6 |
| 20.9 | 4.24 | 6.7 |
| 26.6 | 3.34 | 6.4 |
| 18.4 | 4.81 | 6.4 |
| 30.2 | 2.95 | 6.1 |
| 8.6 | 10.27 | 5.7 |
| 30.7 | 2.90 | 5.2 |
| 20.6 | 4.30 | 5.2 |
| 34.0 | 2.63 | 5.1 |
| 18.7 | 4.72 | 4.9 |
| 16.4 | 5.37 | 4.2 |
| 14.3 | 6.15 | 3.3 |
| 26.0 | 3.42 | 3.2 |
| 4.2 | 20.54 | 3.1 |
| 12.9 | 6.84 | 2.8 |
| 22.2 | 3.99 | 2.6 |
| 10.1 | 8.74 | 2.6 |
| 7.4 | 11.81 | 2.6 |
| 11.2 | 7.84 | 2.4 |
| 19.3 | 4.59 | 2.3 |
| 10.4 | 8.49 | 2.2 |
| 21.7 | 4.07 | 2.1 |
| 28.9 | 3.07 | 2.1 |

TABLE D

| Angle 2-theta | d value, Angstrom | Intensity % |
| --- | --- | --- |
| 20.7 | 4.29 | 100.0 |
| 18.5 | 4.80 | 92.2 |
| 34.1 | 2.63 | 86.4 |
| 16.5 | 5.37 | 82.2 |
| 21.0 | 4.23 | 71.2 |
| 19.4 | 4.58 | 56.1 |
| 17.3 | 5.12 | 52.4 |
| 14.4 | 6.14 | 51.6 |
| 22.7 | 3.91 | 49.0 |
| 29.0 | 3.07 | 46.9 |
| 11.3 | 7.82 | 46.7 |
| 31.8 | 2.81 | 46.5 |
| 36.1 | 2.49 | 45.9 |
| 35.0 | 2.56 | 44.4 |
| 42.0 | 2.15 | 41.4 |
| 7.5 | 11.74 | 39.5 |
| 46.2 | 1.96 | 39.5 |
| 38.0 | 2.37 | 39.1 |
| 8.7 | 10.20 | 39.0 |
| 13.0 | 6.83 | 35.2 |
| 27.7 | 3.22 | 34.6 |
| 38.4 | 2.34 | 32.8 |
| 37.6 | 2.39 | 32.3 |

Example 5

Conversion of a Mixture of Form I and Form II Polymorphs into Form I Polymorph (Hydration in a Glove Bag)

A tray containing a 117.0 g portion of the sodium salt of 2-amino-3-(4-bromobenzoyl)phenylacetic acid, Form I and Form II polymorph mixture, was placed alongside a tray containing water in a glove bag. The bag was sealed under nitrogen and the product allowed to moisturize for 5 h at ambient temperature to give substantially pure Form I polymorph, as indicated by XRPD analysis, of the sodium salt of 2-amino-3-(4-bromobenzoyl)phenylacetic acid, sesquihydrate (117.3 g) as a yellow solid.

Example 6

Process for the Formation of Form I Polymorph (Drying/Hydration Using a Wet Nitrogen Bleed)

Sodium salt of 2-amino-3-(4-bromobenzoyl)phenylacetic acid obtained (5 g), obtained after recrystallization from 10% v/v water in 1,2-dimethoxyethane-20% v/v 1,2-dimethoxyethane in tert-butyl methyl ether, was dried under vacuum (29 in Hg) at 30° C. to 33° C. for 5 h with a slow wet nitrogen gas bleed to give Form I polymorph, as indicated by XRPD analysis, of the sodium salt of 2-amino-3-(4-bromobenzoyl)phenylacetic acid, sesquihydrate (4.4 g) as a yellow solid. These conditions were found to be effective in removing residual organic solvent from the bromfenac sodium while ensuring that the sesquihydrate is obtained (i.e., the water content is not reduced below 1.5 moles water per mole of bromfenac sodium).

Example 7

Formation of a Mixture of Form I and Form II Polymorphs (Hydration Using a Wet Nitrogen Bleed)

Sodium salt of 2-amino-3-(4-bromobenzoyl)phenylacetic acid obtained (26.6 g), obtained after recrystallization from 10% v/v water in 1,2-dimethoxyethane-20% v/v 1,2-dimethoxyethane in tert-butyl methyl ether, was dried under vacuum at 30° C. to 35° C. for 4 h and then under higher vacuum (30-50 mm Hg) at 31° C. to 33° C. for 10 h with a slow wet nitrogen gas bleed to give a mixture of Form I and Form II polymorphs, as indicated by XRPD analysis, of the sodium salt of 2-amino-3-(4-bromobenzoyl)phenylacetic acid, sesquihydrate (26.2 g) as a yellow solid. In contrast to Example 6, these drying conditions were effective to remove sufficient water so as to form bromfenac sodium Form II, which is believed to be a monohydrate of bromfenac sodium.

Example 8

Stability of Form I Polymorph

Sodium salt of 2-amino-3-(4-bromobenzoyl)phenylacetic acid, Form I polymorph (0.6 g) was placed in a drying dish alongside a dish containing water (20 g) in a plastic bag. The bag was sealed under nitrogen and the product allowed to moisturize for 19 h. XRPD and water content analyses of the product (0.6 g) indicated there was no change in polymorphic form.

Example 9

Conversion of Form I and Form II Polymorphs into Form III Polymorph

To sodium salt of 2-amino-3-(4-bromobenzoyl)phenylacetic acid, Form I/Form II polymorph mixture (10 g) was added 5% v/v aqueous 2-propanol (100 mL) and the stirred mixture heated to and maintained at 60-70° C. under nitrogen for 1 h. The mixture was cooled to room temperature and stirred for 1 h. The resulting thick slurry was filtered, washed with 2-propanol (2×10 mL) and dried under vacuum (1.5 mm Hg) at 30° C. to 40° C. for 16 h to give Form III polymorph, as indicated by XRPD analysis, of the sodium salt of 2-amino-3-(4-bromobenzoyl)phenylacetic acid, non-hydrate (9 g) as a yellow solid.

Sodium Salt of
2-amino-3-(4-bromobenzoyl)phenylacetic acid,
Non-Hydrate, Form III Polymorph Analytical Data $^1$H-NMR (300 MHz, DMSO-d$_6$) δ (ppm) 3.29 (2H, s), 6.47 (1H, t, J=7.6 Hz), 7.09 (1H, dd, J=8.1 Hz and 1.1 Hz), 7.17 (1H, d, J=7.1 Hz), 7.49 (2H, d, J=8.3 Hz), 7.70 (2H, d, J=8.7 Hz), 7.89 (2H, bs, exchanges with D$_2$O). $^{13}$C-NMR (300 MHz, DMSO-d$_6$) δ (ppm) 197.0, 174.2, 151.7, 139.4, 135.2, 131.4, 131.1, 130.6, 126.5, 124.4, 116.7, 114.0 and 44.9. LCMS m/z 334.1 and 332.1 [M]$^+$ for carboxylate ion, 290.1, 288.1 (loss of CO$_2$). FT-IR (KBr) 3437, 3327, 3048, 2921, 1623, 1547, 1432, 1411, 1322, 1280, 1237, 1179, 1060, 1005, 963, 938, 840, 823, 798 and 760 cm$^{-1}$. Analysis, calculated for C$_{15}$H$_{11}$BrNO$_3$Na: C, 50.59; H, 3.11; N, 3.93. Br, 22.44. Found: C, 50.62; H, 3.06; N, 3.93; Br, 22.19. Water content by Karl Fischer titration. Found, 0.56%. XRPD characteristic peaks expressed as degrees 2-theta at approximately 12.2, 12.4, 14.1, 15.5, 16.3, 17.8, 18.3, 19.6, 21.6, 22.4, 24.0, 26.3, 26.7, 26.8, 27.2, 28.1, 28.5, 29.7, 30.7, 31.0, 31.7, 34.9, 35.7, 36.2, 38.3, 38.7, 39.4, 43.4, 46.9, 47.8 and 49.0.

What is claimed is:

1. A method of preparing bromfenac sodium Form I, comprising crystallizing or recrystallizing bromfenac sodium a solvent mixture comprising water, at least one dialkoxyalkane, and at least one anti-solvent, wherein the bromfenac sodium Form I is characterized by at least one of the following:
   (a) a powder x-ray diffraction pattern having main peaks expressed as 2-theta at about 4.4, 8.8, 9.4, 12.1, 15.2, 15.9, 17.6, 18.2, 18.8, 20.2, 21.2, 24.7, 28.4, and 32.4 degrees and substantially free of any other physical forms of bromfenac sodium;
   (b) a powder x-ray diffraction pattern in accordance with that shown in FIG. 1 and substantially free of any other physical forms of bromfenac sodium;
   (c) an XRPD d-spacing/% intensity pattern in accordance with that shown in Table A and substantially free of any other physical forms of bromfenac sodium; and
   (d) an FT-IR spectrum in accordance with FIG. 2 and substantially free of any other physical forms of bromfenac sodium.

2. The method of claim 1, wherein the at least one dialkoxyalkane comprises 1,2-dimethoxyethane and the at least one anti-solvent comprises tert-butyl methyl ether.

3. The method of claim 1, wherein the crystallizing or recrystallizing comprises:
   first dissolving the starting bromfenac sodium in a mixture of the water and the at least one dialkoxyalkane to prepare an initial solution; and
   adding the at least one anti-solvent to the initial solution and cooling the resulting mixture to precipitate crystals of the bromfenac sodium Form I.

4. The method of claim 3, wherein:
   the mixture of the water and the at least one dialkoxyalkane is heated to facilitate dissolution of the bromfenac sodium; and
   cooling the resulting mixture comprises cooling to a temperature of from about −10 to about 20° C.

5. The method of claim 1, wherein the crystallizing or recrystallizing further comprises:
   first dissolving the starting bromfenac sodium in a mixture of the water and the at least one dialkoxyalkane to prepare an initial solution;
   allowing the initial solution to settle until an aqueous layer and an organic layer form and separating the organic layer from the aqueous layer;
   filtering the organic layer to remove insoluble impurities;
   concentrating the organic layer to form a wet slurry; and
   combining an anti-solvent with the wet slurry and washing and drying the resulting mixture to recover the bromfenac sodium Form I.

6. The method of claim 1, wherein the bromfenac sodium Form I is characterized solely by (a) a powder x-ray diffraction pattern having main peaks expressed as 2-theta at about 4.4, 8.8, 9.4, 12.1, 15.2, 15.9, 17.6, 18.2, 18.8, 20.2, 21.2, 24.7, 28.4, and 32.4 degrees and is substantially free of any other physical forms of bromfenac sodium.

7. The method of claim 1, wherein the bromfenac sodium Form I is characterized solely by (b) a powder x-ray diffraction pattern in accordance with that shown in FIG. 1 and is substantially free of any other physical forms of bromfenac sodium.

8. The method of claim 1, wherein the bromfenac sodium Form I is characterized solely by (c) an XRPD d-spacing/% intensity pattern in accordance with that shown in Table A and is substantially free of any other physical forms of bromfenac sodium.

9. The method of claim 1, wherein the bromfenac sodium Form I is characterized solely by (d) an FT-IR spectrum in accordance with FIG. 2 and is substantially free of any other physical forms of bromfenac sodium.

10. A method of preparing a pharmaceutical compound comprising bromfenac sodium Form I, comprising crystallizing or recrystallizing bromfenac sodium from a solvent mixture comprising water, at least one dialkoxyalkane, and at least one anti-solvent, wherein the compound does not contain more than 0.15% AUC of any process impurity or bromfenac sodium degradation product, as measured by HPLC, and the bromfenac sodium Form I is characterized by at least one of the following:
    (a) a powder x-ray diffraction pattern having main peaks expressed as 2-theta at about 4.4, 8.8, 9.4, 12.1, 15.2, 15.9, 17.6, 18.2, 18.8, 20.2, 21.2, 24.7, 28.4, and 32.4 degrees and substantially free of any other physical forms of bromfenac sodium;
    (b) a powder x-ray diffraction pattern in accordance with that shown in FIG. 1 and substantially free of any other physical forms of bromfenac sodium;
    (c) an XRPD d-spacing/% intensity pattern in accordance with that shown in Table A and substantially free of any other physical forms of bromfenac sodium; and
    (d) an FT-IR spectrum in accordance with FIG. 2 and substantially free of any other physical forms of bromfenac sodium.

11. The method of claim 10, wherein the at least one dialkoxyalkane comprises 1,2-dimethoxyethane and the at least one anti-solvent comprises tert-butyl methyl ether.

12. The method of claim 10, wherein the crystallizing or recrystallizing comprises:
    first dissolving the starting bromfenac sodium in a mixture of the water and the at least one dialkoxyalkane to prepare an initial solution; and
    adding the at least one anti-solvent to the initial solution and cooling the resulting mixture to precipitate crystals of the bromfenac sodium Form I.

13. The method of claim 12, wherein:
    the mixture of the water and the at least one dialkoxyalkane is heated to facilitate dissolution of the bromfenac sodium; and
    cooling the resulting mixture comprises cooling to a temperature of from about −10 to about 20° C.

14. The method of claim 10, wherein the crystallizing or recrystallizing further comprises:

first dissolving the starting bromfenac sodium in a mixture of the water and the at least one dialkoxyalkane to prepare an initial solution;

allowing the initial solution to settle until an aqueous layer and an organic layer form and separating the organic layer from the aqueous layer;

filtering the organic layer to remove insoluble impurities;

concentrating the organic layer to form a wet slurry; and combining an anti-solvent with the wet slurry and washing and drying the resulting mixture to recover the bromfenac sodium Form I.

15. The method of claim 10, wherein the bromfenac sodium Form I is characterized solely by (a) a powder x-ray diffraction pattern having main peaks expressed as 2-theta at about 4.4, 8.8, 9.4, 12.1, 15.2, 15.9, 17.6, 18.2, 18.8, 20.2, 21.2, 24.7, 28.4, and 32.4 degrees.

16. The method of claim 10, wherein the bromfenac sodium Form I is characterized solely by (b) a powder x-ray diffraction pattern in accordance with that shown in FIG. 1.

17. The method of claim 10, wherein the bromfenac sodium Form I is characterized solely by (c) an XRPD d-spacing/% intensity pattern in accordance with that shown in Table A.

18. The method of claim 10, wherein the bromfenac sodium Form I is characterized solely by (d) an FT-IR spectrum in accordance with FIG. 2.

19. The method of claim 15, wherein the compound does not contain more than 0.10% AUC of any process impurity or bromfenac sodium degradation product, as measured by HPLC.

20. The method of claim 16, wherein the compound does not contain more than 0.10% AUC of any process impurity or bromfenac sodium degradation product, as measured by HPLC.

21. The method of claim 17, wherein the compound does not contain more than 0.10% AUC of any process impurity or bromfenac sodium degradation product, as measured by HPLC.

22. The method of claim 18, wherein the compound does not contain more than 0.10% AUC of any process impurity or bromfenac sodium degradation product, as measured by HPLC.

23. A method of treating a disease or condition selected from the group consisting of at least one of inflammation, reduction of pain, and management of macular edema comprising administering to a human patient in need of treatment a therapeutically effective amount of a pharmaceutical formulation comprising bromfenac sodium Form I and at least one pharmaceutically acceptable excipient therefor, wherein the bromfenac sodium Form I is characterized by at least one of the following:
(a) a powder x-ray diffraction pattern having main peaks expressed as 2-theta at about 4.4, 8.8, 9.4, 12.1, 15.2, 15.9, 17.6, 18.2, 18.8, 20.2, 21.2, 24.7, 28.4, and 32.4 degrees and substantially free of any other physical forms of bromfenac sodium;
(b) a powder x-ray diffraction pattern in accordance with that shown in FIG. 1 and substantially free of any other physical forms of bromfenac sodium;
(c) an XRPD d-spacing/% intensity pattern in accordance with that shown in Table A and substantially free of any other physical forms of bromfenac sodium; and
(d) an FT-IR spectrum in accordance with FIG. 2 and substantially free of any other physical forms of bromfenac sodium.

24. The method of claim 23, wherein the pharmaceutical formulation is in the form of an aqueous liquid preparation formulated for ophthalmic administration and the at least one pharmaceutically acceptable excipient comprises a surfactant.

25. The method of claim 23, wherein the bromfenac sodium Form I is present at a concentration of about 0.01% to about 5% by weight.

26. A method of treating a disease or condition selected from the group consisting of at least one of inflammation, reduction of pain, and management of macular edema comprising administering to a human patient in need of treatment a therapeutically effective amount of a pharmaceutical formulation comprising a pharmaceutical compound comprising bromfenac sodium Form I and at least one pharmaceutically acceptable excipient therefor, wherein the compound does not contain more than 0.15% AUC of any process impurity or bromfenac sodium degradation product, as measured by HPLC, and the bromfenac sodium Form I is characterized by at least one of the following:
(a) a powder x-ray diffraction pattern having main peaks expressed as 2-theta at about 4.4, 8.8, 9.4, 12.1, 15.2, 15.9, 17.6, 18.2, 18.8, 20.2, 21.2, 24.7, 28.4, and 32.4 degrees and substantially free of any other physical forms of bromfenac sodium;
(b) a powder x-ray diffraction pattern in accordance with that shown in FIG. 1 and substantially free of any other physical forms of bromfenac sodium;
(c) an XRPD d-spacing/% intensity pattern in accordance with that shown in Table A and substantially free of any other physical forms of bromfenac sodium; and
(d) an Fr-IR spectrum in accordance with FIG. 2 and substantially free of any other physical forms of bromfenac sodium.

27. The method of claim 26, wherein the pharmaceutical formulation is in the form of an aqueous liquid preparation formulated for ophthalmic administration and the at least one pharmaceutically acceptable excipient comprises a surfactant.

28. The method of claim 26, wherein the pharmaceutical compound is present at a concentration of about 0.01% to about 5% by weight.

29. The method of claim 26, wherein the pharmaceutical compound is substantially free of any other physical forms of bromfenac sodium.

30. The method of claim 26, wherein the compound does not contain more than 0.10% AUC of any process impurity or bromfenac sodium degradation product, as measured by HPLC.

31. Bromfenac sodium Form I characterized by at least one of the following:
(a) a powder x-ray diffraction pattern having main peaks expressed as 2-theta at about 4.4, 8.8, 9.4, 12.1, 15.2, 15.9, 17.6, 18.2, 18.8, 20.2, 21.2, 24.7, 28.4, and 32.4 degrees and substantially free of any other physical forms of bromfenac sodium;
(b) a powder x-ray diffraction pattern in accordance with that shown in FIG. 1 and substantially free of any other physical forms of bromfenac sodium;
(c) an XRPD d-spacing/% intensity pattern in accordance with that shown in Table A and substantially free of any other physical forms of bromfenac sodium; and
(d) an FT-IR spectrum in accordance with FIG. 2 and substantially free of any other physical forms of bromfenac sodium
made according to the method of claim 1.

32. The pharmaceutical compound comprising bromfenac sodium Form I wherein the compound does not contain more than 0.15% AUC of any process impurity or bromfenac sodium degradation product, as measured by HPLC, and the bromfenac sodium Form I is characterized by at least one of the following:

(a) a powder x-ray diffraction pattern having main peaks expressed as 2-theta at about 4.4, 8.8, 9.4, 12.1, 15.2, 15.9, 17.6, 18.2, 18.8, 20.2, 21.2, 24.7, 28.4, and 32.4 degrees and substantially free of any other physical forms of bromfenac sodium;

(b) a powder x-ray diffraction pattern in accordance with that shown in FIG. 1 and substantially free of any other physical forms of bromfenac sodium;

(c) an XRPD d-spacing/% intensity pattern in accordance with that shown in Table A and substantially free of any other physical forms of bromfenac sodium; and (d) an FT-IR spectrum in accordance with FIG. 2 and substantially free of any other physical forms of bromfenac sodium made according to the method of claim 10.

* * * * *